(12) United States Patent
Choi et al.

(10) Patent No.: US 10,610,467 B2
(45) Date of Patent: Apr. 7, 2020

(54) LIGHTENING COMPOSITION COMPRISING GINSENG-DERIVED EXOSOME-LIKE VESICLES

(71) Applicant: AMOREPACIFIC CORPORATION, Seoul (KR)

(72) Inventors: Suh-Yeon Choi, Yongin-si (KR); Eun-Jeong Choi, Yongin-si (KR); Bum-Ho Bin, Yongin-si (KR); Kyeonghwan Hwang, Yongin-si (KR); Eun-Gyung Cho, Yongin-si (KR); Tae Ryong Lee, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 162 days.

(21) Appl. No.: 15/760,819

(22) PCT Filed: Sep. 23, 2016

(86) PCT No.: PCT/KR2016/010605
§ 371 (c)(1),
(2) Date: Mar. 16, 2018

(87) PCT Pub. No.: WO2017/052242
PCT Pub. Date: Mar. 30, 2017

(65) Prior Publication Data
US 2018/0263871 A1 Sep. 20, 2018

(30) Foreign Application Priority Data

Sep. 23, 2015 (KR) ........................ 10-2015-0134534
Aug. 17, 2016 (KR) ........................ 10-2016-0104381

(51) Int. Cl.
*A61K 8/14* (2006.01)
*A61Q 19/02* (2006.01)
*A61K 8/9789* (2017.01)
*A61K 36/258* (2006.01)

(52) U.S. Cl.
CPC .............. *A61K 8/14* (2013.01); *A61K 8/9789* (2017.08); *A61K 36/258* (2013.01); *A61Q 19/02* (2013.01); *A61K 2800/413* (2013.01)

(58) Field of Classification Search
CPC ...... A61K 8/14; A61K 8/9789; A61K 36/258; A61K 2800/413; A61Q 19/02
See application file for complete search history.

(56) References Cited

U.S. PATENT DOCUMENTS 8,709,511 B2  4/2014  Yeom et al.
2011/0085996 A1  4/2011  Yeom et al.

FOREIGN PATENT DOCUMENTS

| CN | 102329702 | * | 1/2012 |
| CN | 103462846 A | | 12/2013 |
| CN | 103479682 A | | 1/2014 |
| CN | 104825365 A | | 8/2015 |
| KR | 10-2009-0130801 A | | 12/2009 |
| WO | 2005/067885 A1 | | 7/2005 |

OTHER PUBLICATIONS

Li, CN 102329702, published: Jan. 25, 2012, English translation obtained on Nov. 22, 2019.*
International Search Report from PCT/KR20016/010605 (dated Jan. 13, 2017).
Written Opinion from PCT/KR20016/010605 (dated Jan. 13, 2017).
Ju et al., "Grape Exosome-like Nanoparticles Induce Intestinal Stem Cells and Protect Mice from DSS-induced Colitis" Molecular Therapy, 21(7):1345-1357 (2013).
Halperin et al., "Ultrastructural Changes during Growth and Embryogenesis in Carrot Cell Cultures", J. Ultrastructure Research, 18:428-443 (1967).
Marchant et al., "Membrane Systems Associated with the Plasmalemma of Plant Cells", Annals of Botany, 32(127):457-471 (Jul. 1968).
Marchant et al., "The Ultrastructural Basis of Hyphal Growth", New Phytol., 66:623-629 (1967).
Ohno et al., "Roles of exosomes and microvesicles in disease pathogenesis", Advanced Drug Delivery Reviews, 65(3):398-401 (2013).
Loyer et al., "Microvesicles as Cell-Cell Messengers in Cardiovascular Diseases", Circulation Research, 114(2):345-353 (Jan. 2014).
An et al., "Multivesicular bodies participate in a cell wall-associated defence response in barley leaves attacked by the pathogenic powdery mildew fungus," Cell Microbiology, 2006, vol. 8, No. 6, pp. 1009-1019.
Regente et al., "Apoplastic exosome-like vesicles: A new way of protein secretion in plants?" Plant Signaling & Behavior, 2012, vol. 7, No. 5, pp. 544-546.
Extended European Search Report from European Application No. 16848967.2, dated Apr. 23, 2019.
Office Action issued in corresponding Taiwanese Patent Application No. 105129274, dated Feb. 10, 2020. Y references are only considered; the remaining in not in English.
Kwangmi Kim, "Effect of ginseng and ginsenosides on melanogenesis and their mechanism of action", Journal of Ginseng Research, J Ginseng Res, 2015, vol. 39, pp.1-6.

* cited by examiner

*Primary Examiner* — Ali Soroush
*Assistant Examiner* — Genevieve S Alley
(74) *Attorney, Agent, or Firm* — Merchant & Gould P.C.

(57) ABSTRACT

Disclosed are: a lightening composition comprising ginseng-derived exosome-like vesicles; and a method for producing the ginseng-derived exosome-like vesicles. The ginseng-derived exosome-like vesicles may have a diameter of between 20 and 500 nm, and may be isolated from ginseng root. Because the composition comprises the ginseng-derived exosome-like vesicles as an active ingredient, said composition is effective in preventing, improving or treating skin pigmentation conditions such as liver spots, freckles, lentigo, birth marks and melanoma by effectively suppressing the production of melanin.

12 Claims, 4 Drawing Sheets

LIGHTENING COMPOSITION COMPRISING GINSENG-DERIVED EXOSOME-LIKE VESICLES

This application is a U.S. National Stage Application under 35 U.S.C. § 371 of International Patent Application No. PCT/KR2016/010605 filed Sep. 23, 2016, which claims the benefit of priority to Korean Patent Application No. 10-2016-0104381 filed Aug. 17, 2016 and Korean Patent Application No. 10-2015-0134534 filed Sep. 23, 2015, the disclosures of all of which are hereby incorporated by reference in their entireties. The International Application was published in Korean on Mar. 30, 2017 as WO 2017/052242.

TECHNICAL FIELD

Disclosed in the present disclosure are a composition for skin whitening containing ginseng-derived exosome-like vesicles and a method for preparing the ginseng-derived exosome-like vesicles.

BACKGROUND ART

Most animal cells have the ability of secreting cell-derived extracellular vesicles of various sizes and compositions. These extracellular vesicles are found in all biological fluids, including blood, urine, saliva and cultured medium of cell cultures (Loyer X, Vion A C, Tedgui A, Boulanger C M. Microvesicles as cell-cell messengers in cardiovascular diseases. *Circ Res* 2014; 114: 345-53; Ohno S, Ishikawa A, Kuroda M. Roles of exosomes and microvesicles in disease pathogenesis. *Adv Drug Deliv Rev* 2013; 65: 398-401).

Extracellular vesicles are membrane structure vesicles with diameters from about 20 nm to about 5 μm. They differ in sizes and compositions and include various species such as exosomes (about 30-100 nm), ectosomes, microvesicles (about 100-1,000 nm), microparticles, etc.

The different types of the extracellular vesicles are distinguished based on their origin, diameter, density in sucrose, shape, precipitation rate, lipid composition, protein marker, secretion type (i.e., whether they are induced by signals or naturally produced), etc. For example, microvesicles are membrane vesicles ranging from about 100 to 1,000 nm with irregular shapes. They originate from the plasma membrane and are known to contain integrins, selectins, markers including CD40 ligand, and lipids including phosphatidylserines. And, exosomes are the smallest membrane vesicles ranging from about 30 to 100 nm (<200 nm) with a cups shape. They originate from endosomes and are known to contain tetraspanins such as CD63 and CD9, markers including TSG101 and ESCRT, and lipids including cholesterols, sphingomyelins, ceram ides and phosphatidylserines.

The extracellular vesicles reflect the state of the cells (donor cells) from which they are secreted, exhibit various biological activities depending on the cells from which they are secreted, and play an important role in cell-to-cell interactions as they transfer genetic materials and proteins between cells.

In plants too, small vesicles are released to the extracellular space as a result of fusion between the plasma membrane and multivesicular bodies, and vesicles in multivesicular bodies are observed in the extracellular space of plant cells of various species (Marchant R, Peat A, Banbury G H. The ultrastructural basis of hyphal growth. *New Phytol.* 1967; 66: 623-629; Halperin W, Jensen W A. Ultrastructural changes during growth and embryogenesis in carrot cell cultures. *J Ultrastruct Res.* 1967; 18: 428-443; Marchant R, Robards A W. Membrane systems associated with the plasmalemma of plant cells. *Ann Bot.* 1968; 32: 457-471). Also, it was recently reported that the exosome-like nanoparticles derived from plant cells are similar to the exosomes derived from mammalian cells in nanosized vesicular structure and nanoparticle composition (An, Q, Hückelhoven, R, Kogel, K H and van Bel, A J (2006). Multivesicular bodies participate in a cell wall-associated defence response in barley leaves attacked by the pathogenic powdery mildew fungus. *Cell Microbiol* 8: 1009-1019; Regente, M, Pinedo, M, Elizalde, M and de la Canal, L (2012). Apoplastic exosome-like vesicles: a new way of protein secretion in plants? *Plant Signal Behav* 7: 544-546).

Exosomes have been used mainly as biomarkers. However, technologies for using exosomes for specific purposes based on the intrinsic efficacy of the exosomes have not been developed. In particular, little is known about the specific use of exosome-like membrane structure vesicles derived from plant cells. As for ginseng, although the skin whitening effect of ginseng-derived extracts or ingredients thereof has been reported, the skin whitening effect of ginseng-derived exosome-like membrane structure vesicles has not been reported. The prior art about ginseng extracts is disclosed in Korean Patent Publication No. 10-2009-0130801.

DISCLOSURE

Technical Problem

In an aspect, the present disclosure is directed to providing a composition for skin whitening, which contains a ginseng-derived exosome-like vesicle, not a ginseng extract, as an active ingredient.

In another aspect, the present disclosure is directed to providing a method for preparing the ginseng-derived exosome-like vesicle.

Technical Solution

The present disclosure provides a composition for skin whitening, which contains a ginseng-derived exosome-like vesicle as an active ingredient.

In an aspect, the exosome-like vesicle may be isolated from ginseng root.

In another aspect, the exosome-like vesicle may have a diameter of 20-500 nm.

In another aspect, the exosome-like vesicle may be precipitated by ultracentrifugation of the extracellular fluid of ginseng at 100,000×g or higher.

In another aspect, the exosome-like vesicle may have a buoyant density of 1.00-1.20 g/mL in iodixanol.

In another aspect, the active ingredient may inhibit melanin production.

In another aspect, the active ingredient may prevent, improve or treat one or more skin pigmentation disease selected from a group consisting of melasma, freckle, lentigo, nevus, melanoma, drug-induced pigmentation, post-inflammatory pigmentation and dermatitis-induced pigmentation.

The present disclosure also provides a method for preparing the ginseng-derived exosome-like vesicle, which includes: (1) a step of obtaining a juice by squeezing ginseng; (2) a step of centrifuging the juice and obtaining a supernatant by removing the remnant; and (3) a step of obtaining an exosome-like vesicle by ultracentrifuging the supernatant.

In an aspect, the centrifugation in the step (2) may be performed at 500-3,000×g for 10-30 minutes.

In another aspect, the ultracentrifugation in the step (3) may be performed using a sucrose cushion density gradient and an iodixanol density gradient.

In another aspect, the ultracentrifugation in the step (3) may be performed at 100,000-200,000×g for 1-6 hours.

In another aspect, in the step (3), the exosome-like vesicle may be obtained by ultracentrifuging the supernatant and then separating a fraction having a buoyant density of 1.00-1.20 g/mL in iodixanol.

Advantageous Effects

In an aspect, the present disclosure provides an effect of providing a composition for skin whitening, which contains a ginseng-derived exosome-like vesicle as an active ingredient.

In another aspect, the present disclosure provides an effect of providing a method for preparing the ginseng-derived exosome-like vesicle.

BEST MODE

Hereinafter, the present disclosure is described in detail.

The present disclosure provides a composition for skin whitening, which contains a ginseng-derived exosome-like vesicle as an active ingredient. The present disclosure provides a composition for skin whitening, which contains a ginseng-derived exosome-like vesicle, specifically an exosome-like vesicle derived from the extracellular fluid of ginseng, not a ginseng-derived extract, as an active ingredient.

In an exemplary embodiment, the ginseng may be one or more selected from a group consisting of the seed, root, stem, leaf and fruit of a plant in the genus *Panax*. Specifically, the plant in the genus *Panax* may be Korean ginseng (*Panax ginseng*), American ginseng (*Panax quinquefolium*), notoginseng (*Panax notoginseng*), Japanese ginseng (*Panax japonicum*), dwarf ginseng (*Panax trifolium*), Himalayan ginseng (*Panax pseudoginseng*), Vietnamese ginseng (*Panax vietnamensis*), etc. It is not limited in species, type, processing, growth environment, etc. and may include red ginseng, fresh ginseng, white ginseng, cultured ginseng or wild ginseng including woods-grown ginseng, mountain-grown ginseng and cultured-root of wild ginseng.

In the present disclosure, the "exosome-like vesicle" refers to a nanosized extracellular vesicle secreted by a cell to the extracellular space. The vesicle includes an exosome and is used in the broadest concept, including an vesicle similar in a nanosized vesicular structure and a composition with the exosome.

The exosome-like vesicle is secreted to the extracellular space as a result of fusion between the plasma membrane and the multivesicular body by exocytosis. The exosome-like vesicle is divided into inside and outside by a lipid bilayer and indirectly reflects the properties and state of the cell because it contains membrane lipids, membrane proteins, genetic materials and cytoplasmic components. Also, the exosome-like vesicle serves as an extracellular transporter mediating cell-cell communication by binding to other cells and tissues and transferring membrane components, mRNAs, miRNAs, proteins (growth hormones, cytokines, etc.), etc. to acceptor cells.

In the present disclosure, the "ginseng-derived exosome-like vesicle" refers to a nanosized exosome-like vesicle secreted by ginseng cells. The exosome-like vesicle may be isolated from the extracellular fluid of ginseng and the exosome-like vesicle may be physically isolated entirely or partially from existing tissues or cells.

In an exemplary embodiment, the exosome-like vesicle may be isolated from ginseng root.

In an aspect, the exosome-like vesicle may be an extracellular vesicle having a diameter of 20-500 nm. In another aspect, the exosome-like vesicle may be an extracellular vesicle having a diameter of 20 nm or larger, 30 nm or larger, 40 nm or larger, 50 nm or larger, 60 nm or larger, 70 nm or larger, 80 nm or larger, 90 nm or larger or 100 nm or larger and 500 nm or smaller, 450 nm or smaller, 400 nm or smaller, 350 nm or smaller, 300 nm or smaller, 250 nm or smaller, 200 nm or smaller, 150 nm or smaller or 100 nm or smaller.

In another aspect, the exosome-like vesicle may be precipitated by ultracentrifuging the extracellular fluid of ginseng at 100,000×g or higher, specifically at 100,000-200,000×g or 100,000×g.

In another aspect, the exosome-like vesicle may have a buoyant density of 1.00-1.20 g/mL, 1.03-1.20 g/mL or 1.06-1.20 g/mL in iodixanol. The buoyant density refers to a density measured by density gradient centrifugation.

In another aspect, the membrane component of the exosome-like vesicle may be chemically or physically modified so as to effectively perform the desired function in a target cell. For example, the membrane component of the exosome-like vesicle may be chemically modified using a thiol group (—SH) or an amine group (—$NH_2$) or by chemically binding a inducing substance, a fusogen, polyethylene glycol to the exosome-like vesicle.

In an exemplary embodiment, the exosome-like vesicle may be isolated by one or more method selected from a group consisting of ultracentrifugation, differential centrifugation, equilibrium density centrifugation, density gradient, filtration, dialysis and free-flow electrophoresis, although not being limited thereto.

Density gradient is a method which is the most frequently used when separating materials with different densities. The exosome-like vesicles according to the present disclosure can be isolated by density gradient because of different densities. As a specific example, density gradient separation materials such as Ficoll, glycerol, sucrose, cesium chloride, iodixanol, etc. may be used, although not being limited thereto. In an aspect, the density gradient may be used together with ultracentrifugation, etc. In another aspect, gel filtration or ultrafiltration may be used to separate the exosome-like vesicles. In another aspect, dialysis may be used instead of filtration in order to remove small-sized molecules. In another aspect, free-flow electrophoresis may be used.

In an exemplary embodiment, the ginseng-derived exosome-like vesicle may be obtained by a method which includes: (1) a step of obtaining a juice containing the extracellular fluid of ginseng from ginseng; (2) a step of centrifuging the juice and obtaining a supernatant by removing the remnant; and (3) a step of obtaining an exosome-like vesicle by ultracentrifuging the supernatant.

In an exemplary embodiment, the juice in the step (1) is a liquid squeezed from ginseng and may be obtained by mechanical degradation, treatment with chemicals, etc. In an aspect, the juice may be obtained by squeezing ginseng and the squeezing may be adequately performed by those of ordinary skill according to a method known in the art.

In an exemplary embodiment, the centrifugation in the step (2) may be performed at 500-3,000×g for 10-30 minutes. The speed or time of the centrifugation may be varied by stages.

In another aspect, the ultracentrifugation in the step (3) may be performed using a sucrose cushion density gradient and an iodixanol density gradient.

In another aspect, the ultracentrifugation in the step (3) may be performed at 100,000-200,000×g for 1-6 hours. The speed or time of the centrifugation may be varied by stages.

In another aspect, the ultracentrifugation in the step (3) may be performed at 100,000-200,000×g for 1-6 hours using a sucrose cushion density gradient and an iodixanol density gradient.

In another aspect, in the step (3), the exosome-like vesicle may be obtained by ultracentrifuging the supernatant and then separating a fraction having a buoyant density of 1.00-1.20 g/mL. The separated fraction may be diluted with a buffer and then ultracentrifuged. Specifically, a pelletized exosome-like vesicle having a diameter 20-500 nm may be isolated by ultracentrifuging at 100,000×g for 2 hours.

In an exemplary embodiment, the active ingredient provides an effect of preventing, treating or improving skin damage or a skin disease directly or indirectly associated with melanin increase. That is to say, the active ingredient provides an effect of preventing, treating or improving a disease caused by excessive melanin production by effectively inhibiting melanin production.

In another aspect, the present disclosure provides a method for enhancing skin whitening, which includes administering the ginseng-derived exosome-like vesicle of an amount effective for enhancing skin whitening to a subject in need thereof.

In another aspect, the present disclosure provides a method for suppressing melanin production, which includes administering the ginseng-derived exosome-like vesicle of an amount effective for suppressing melanin production to a subject in need thereof.

In another aspect, the present disclosure provides a method for preventing, treating and/or improving skin damage or a skin disease directly or indirectly associated with melanin increase and/or a disease caused by excessive melanin production, which includes administering the ginseng-derived exosome-like vesicle of an amount effective for preventing, treating and/or improving the skin damage or skin disease directly or indirectly associated with melanin increase and/or the disease caused by excessive melanin production to a subject in need thereof.

In another aspect, the present disclosure provides the ginseng-derived exosome-like vesicle for enhancing skin whitening of a subject.

In another aspect, the present disclosure provides the ginseng-derived exosome-like vesicle for suppressing melanin production of a subject.

In another aspect, the present disclosure provides the ginseng-derived exosome-like vesicle for preventing, treating and/or improving skin damage or a skin disease directly or indirectly associated with melanin increase and/or a disease caused by excessive melanin production.

In another aspect, the present disclosure provides a use for preparing a composition containing the ginseng-derived exosome-like vesicle for enhancing skin whitening of a subject.

In another aspect, the present disclosure provides a use for preparing a composition containing the ginseng-derived exosome-like vesicle for suppressing melanin production of a subject.

In another aspect, the present disclosure provides a use for preparing a composition containing the ginseng-derived exosome-like vesicle for preventing, treating and/or improving skin damage or a skin disease directly or indirectly associated with melanin increase and/or a disease caused by excessive melanin production.

In an exemplary embodiment, the ginseng-derived exosome-like vesicle may be applied or administered to a subject in the form of a pharmaceutical composition, a cosmetic composition or a food composition In an exemplary embodiment, the ginseng-derived exosome-like vesicle may be applied or administered to the skin of a subject.

In an exemplary embodiment, the disease caused by excessive melanin production may be one or more selected from a group consisting of melasma, freckle, age spot, blemish, epidermal melanocytic lesion, milk coffee spot (cafe's au lait macule), Becker's nevus, nevus spilus, lentigo, dermal melanocytic lesion, Mongolian spot, nevus of Ota, acquired bilateral nevus of Ota-like macule, nevus of Ito, blue nevus, melanocytic nevus, junctional nevus, compound nevus, intradermal nevus, halo nevus, congenital melanocytic nevus, Spitz nevus, dysplastic nevus, melanoma, lentigo maligna melanoma, superficial spreading melanoma, acral lentiginous melanoma, nodular melanoma, pigmented basal cell carcinoma, pigmented dermatofibromas, pigmented dermoid cyst, pigmented keloid and pigmented keratoacanthomas.

In an exemplary embodiment, the composition may prevent, improve or treat one or more skin pigmentation disease selected from a group consisting of melasma, freckle, lentigo, nevus, melanoma, drug-induced pigmentation, post-inflammatory pigmentation and dermatitis-induced pigmentation, occurring topically on the skin due to increased melanin production.

In another aspect, the present disclosure provides a method for preventing, improving and/or treating one or more skin pigmentation disease selected from a group consisting of melasma, freckle, lentigo, nevus, melanoma, drug-induced pigmentation, post-inflammatory pigmentation and dermatitis-induced pigmentation, occurring topically on the skin due to increased melanin production, which includes administering an effective amount of the ginseng-derived exosome-like vesicle to a subject in need thereof.

In another aspect, the present disclosure provides the ginseng-derived exosome-like vesicle for preventing, improving and/or treating one or more skin pigmentation disease selected from a group consisting of melasma, freckle, lentigo, nevus, melanoma, drug-induced pigmentation, post-inflammatory pigmentation and dermatitis-induced pigmentation, occurring topically on the skin due to increased melanin production.

In another aspect, the present disclosure provides a use for preparing a composition containing the ginseng-derived exosome-like vesicle for preventing, improving and/or treating one or more skin pigmentation disease selected from a group consisting of melasma, freckle, lentigo, nevus, melanoma, drug-induced pigmentation, post-inflammatory pigmentation and dermatitis-induced pigmentation, occurring topically on the skin due to increased melanin production.

In an exemplary embodiment, the composition may be a freeze-dried formulation. The composition may be a freeze-dried formulation contained in a sealed packaging material or container so that it can be used readily (ready-to-use).

The present disclosure also provides a kit for skin whitening, for suppressing melanin production or for preventing, improving or treating a skin pigmentation disease, which contains: a freeze-dried composition containing the ginseng-derived exosome-like vesicle as an active ingredient; and sterile water or purified water. The kit may be contained in a sealed packaging material or container so that it can be used readily (ready-to-use).

In an exemplary embodiment, the composition may be a pharmaceutical composition.

The pharmaceutical composition may contain, in addition to the ginseng-derived exosome-like vesicle, a pharmaceutical adjuvant such as an antiseptic, a stabilizer, a wetting agent, an emulsification promoter, a salt and/or buffer for control of osmotic pressure, etc. and other therapeutically useful substances and may be prepared into various formulations for oral or parenteral administration according to common methods.

The formulation for oral administration may be, for example, a tablet, a pill, a hard or soft capsule, a liquid, a suspension, an emulsion, a syrup, a powder, a dust, a fine granule, a granule, a pellet, etc. and these formulations may contain, in addition to the active ingredient, a surfactant, a diluent (e.g., lactose, dextrose, sucrose, mannitol, sorbitol, cellulose and glycine), a lubricant (e.g., silica, talc, stearic acid and a magnesium or calcium salt thereof and polyethylene glycol). The tablet may further contain a binder such as magnesium aluminum silicate, starch paste, gelatin, tragacanth, methyl cellulose, sodium carboxymethyl cellulose and polyvinylpyrrolidine and may contain a pharmaceutical additive such as a disintegrant, e.g., starch, agar or alginic acid or a sodium salt thereof, an absorbent, a colorant, a flavor, a sweetener, etc. as occasion demands. The tablet may be prepared by a common mixing, granulation or coating method.

The formulation for parenteral administration may be a formulation for transdermal administration, e.g., an injection, a drip, an ointment, a lotion, a gel, a cream, a spray, a suspension, an emulsion, a suppository, a patch, etc., although not being limited thereto.

Determination of the administration dosage of the active ingredient is within the level of those of ordinary skill. A daily administration dosage may vary depending on various factors such as the stage of the disease to be treated, age, health condition, presence of complication, etc. In an aspect, the composition may be administered at a daily dosage of 1 µg/kg to 200 mg/kg, more specifically 50 µg/kg to 50 mg/kg, 1-3 times a day. However, the administration dosage does not limit the scope of the present disclosure by any means.

The pharmaceutical composition may be a formulation for external application to the skin. The formulation for external application to the skin includes any formulation that can be applied externally on the skin and various types of medical formulations may be included therein.

In an exemplary embodiment, the composition may be a cosmetic composition.

The cosmetic composition may contain, in addition to the ginseng-derived exosome-like vesicle, a functional additive and an ingredient commonly included in a cosmetic composition. The functional additive may include an ingredient selected from a group consisting of a water-soluble vitamin, an oil-soluble vitamin, a polypeptide, a polysaccharide, a sphingolipid and a seaweed extract. In addition, an oil, a fat, a humectant, an emollient, a surfactant, an organic or inorganic pigment, an organic powder, a UV absorbent, an antiseptic, a sterilizer, an antioxidant, a plant extract, a pH control agent, an alcohol, a colorant, a flavor, a blood circulation promoter, a cooling agent, an antiperspirant, purified water, etc. may be further contained.

The formulation of the cosmetic composition is not specially limited and may be selected adequately depending on purposes. For example, it may be prepared into one or more formulation selected from a group consisting of a skin lotion, a skin softener, a skin toner, an astringent, a lotion, a milk lotion, a moisturizing lotion, a nourishing lotion, a massage cream, a nourishing cream, a moisturizing cream, a hand cream, a foundation, an essence, a nourishing essence, a pack, a soap, a cleansing foam, a cleansing lotion, a cleansing cream, a body lotion and a body cleanser, although not being limited thereto.

When the formulation of the present disclosure is a paste, a cream or a gel, an animal fiber, a plant fiber, a wax, paraffin, starch, tragacanth, a cellulose derivative, polyethylene glycol, silicone, bentonite, silica, talc, zinc oxide, etc. may be used as a carrier ingredient.

When the formulation of the present disclosure is a powder or a spray, lactose, talc, silica, aluminum hydroxide, calcium silicate, polyamide powder, etc. may be used as a carrier ingredient. In particular, when the formulation is a spray, it may further contain a propellant such as chlorofluorohydrocarbon, propane/butane or dimethyl ether.

When the formulation of the present disclosure is a solution or an emulsion, a solvent, a solubilizer or an emulsifier may be used as a carrier ingredient. For example, water, ethanol, isopropanol, ethyl carbonate, ethyl acetate, benzyl alcohol, benzyl benzoate, propylene glycol, 1,3-butyl glycol oil, a glycerol aliphatic ester, polyethylene glycol or a fatty acid ester of sorbitan may be used.

When the formulation of the present disclosure is a suspension, a liquid diluent such as water, ethanol or propylene glycol, a suspending agent such as ethoxylated isostearyl alcohol, polyoxyethylene sorbitol ester and polyoxyethylene sorbitan ester, microcrystalline cellulose, aluminum metahydroxide, bentonite, agar, tragacanth, etc. may be used as a carrier ingredient.

When the formulation of the present disclosure is a surfactant-containing cleanser, an aliphatic alcohol sulfate, an aliphatic alcohol ether sulfate, sulfosuccinic monoester, isethionate, an imidazolinium derivative, methyl taurate, sarcosinate, a fatty acid amide ether sulfate, an alkyl amidobetaine, an aliphatic alcohol, a fatty acid glyceride, a fatty acid diethanolamide, a vegetable oil, a lanolin derivative, an ethoxylated glycerol fatty acid ester, etc. may be used as a carrier ingredient.

In an exemplary embodiment, the composition may be a food composition.

The food composition may be a liquid or solid formulation. For example, it may be in the form of various foods, beverages, gums, teas, vitamin mixtures, supplementary health foods, etc. and may be formulated as a powder, a granule, a tablet, a capsule or a drink. Each formulation of the food composition may be prepared by those skilled in the art without difficulty by mixing the active ingredient with ingredients commonly used in the art depending on purposes. A synergic effect may be achieved when the active ingredient is used together with other ingredients.

Liquid ingredients that may be contained in the food composition in addition to the active ingredient are not particularly limited. Various flavors, natural carbohydrates, etc. may be further contained as in common drinks. The natural carbohydrate may be a monosaccharide, a disaccharide such as glucose, fructose, etc., a polysaccharide such as maltose, sucrose, etc., a common sugar such as dextrin, cyclodextrin, etc. or a sugar alcohol such as xylitol, sorbitol, erythritol, etc. As the flavor, a natural flavor (thaumatin, stevia extract (e.g., rebaudioside A, glycyrrhizin, etc.) or a synthetic flavor (e.g., saccharin, aspartame, etc.) may be used. The natural carbohydrate may be contained in an amount of generally about 1-20 g, specifically about 5-12 g, per 100 mL of the composition according to the present disclosure.

In an aspect, the food composition may contain various nutrients, vitamins, minerals (electrolytes), flavors such as synthetic flavors and natural flavors, colorants, extenders (cheese, chocolate, etc.), pectic acid and salts thereof, alginic acid and salts thereof, organic acids, protective colloidal thickeners, pH control agents, stabilizers, antiseptics, glycerin, alcohols, carbonating agents used in carbonated drinks, etc. In another aspect, pulps for preparing natural fruit juice and vegetable drinks may be contained. These ingredients may be used independently or in combination. These additives may be used in an amount of about 0.001-20 parts by weight per 100 parts by weight of the composition according to the present disclosure, although not being limited thereto.

MODE FOR INVENTION

Hereinafter, the present disclosure will be described in detail through examples. However, the following examples are for illustrative purposes only and the scope of the present disclosure is not limited by the examples.

Example 1

Isolation of Ginseng-Derived Exosome-Like Vesicles (Step 1) First, a juice containing the extracellular fluid of ginseng root was prepared by squeezing 4-year-old ginseng root.

(Step 2) A supernatant was obtained by centrifuging the juice at 4° C. and 500×g for 10 minutes. Then, a supernatant was obtained by centrifuging it again at 4° C. and 3,000×g for 20 minutes.

(Step 3) After sequentially adding 0.5 mL of 2.5 M sucrose, 1 mL of 0.8 M sucrose and 32 mL of the supernatant with impurities removed to a 35-mL ultracentrifugation tube, the tube was ultracentrifuged at 4° C. and 100,000×g for 2 hours. After the ultracentrifugation, exosome-like vesicles of ginseng root were located between the 2.5 M sucrose layer and the 0.8 M sucrose layer due to their densities. Therefore, the layer in which the exosome-like vesicles of ginseng root were contained was separated by removing the solution from the top side of the tube.

Figure 1:
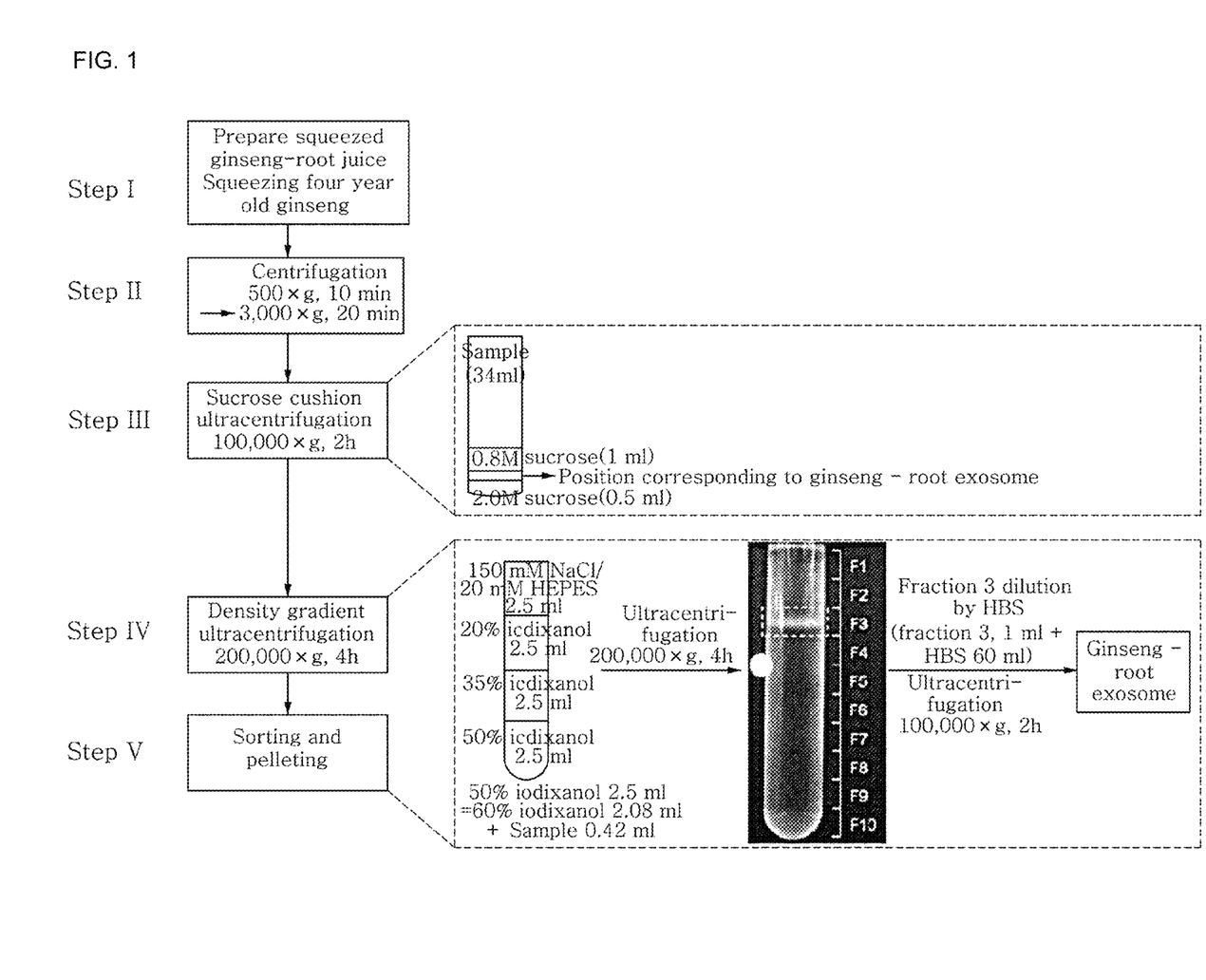
FIG. 1 shows a process of isolating exosome-like vesicles from a juice of ginseng root according to an exemplary embodiment of the present disclosure.

(Step 4) The separated layer containing the exosome-like vesicles of ginseng root was subjected to density gradient ultracentrifugation. Specifically, 0.42 mL of the separated layer containing the exosome-like vesicles of ginseng root was mixed with 2.08 mL of 60% iodixanol. The resulting 2.5 mL of 50% iodixanol was added to a 12-mL ultracentrifugation tube. Then, ultracentrifugation was performed at 4° C. and 200,000×g for 4 hours after sequentially adding 2.5 mL of 35% iodixanol, 2.5 mL of 20% iodixanol and 2.5 mL of 150 mM NaCl/20 mM HEPES to the tube. Subsequently, 1-mL fractions were obtained from the top side of the tube and fraction 3 (1.08 g/mL) corresponding to the density of exosome-like vesicles was taken by measuring densities (see FIG. 1).

(Step 5) The obtained fraction 3 was diluted in 60 mL of HBS (HEPES-buffered saline) and added to a 70-mL ultracentrifugation tube. Then, pelletized ginseng-derived exosome-like vesicles were obtained by ultracentrifuging at 4° C. and 100,000×g for 2 hours.

Test Example 1. Transmission Electron Microscopic Analysis of Ginseng-Derived Exosome-Like Vesicles The size and shape of the ginseng-derived exosome-like vesicles obtained in Example 1 were analyzed by transmission electron microscopy (TEM).

Figure 2:
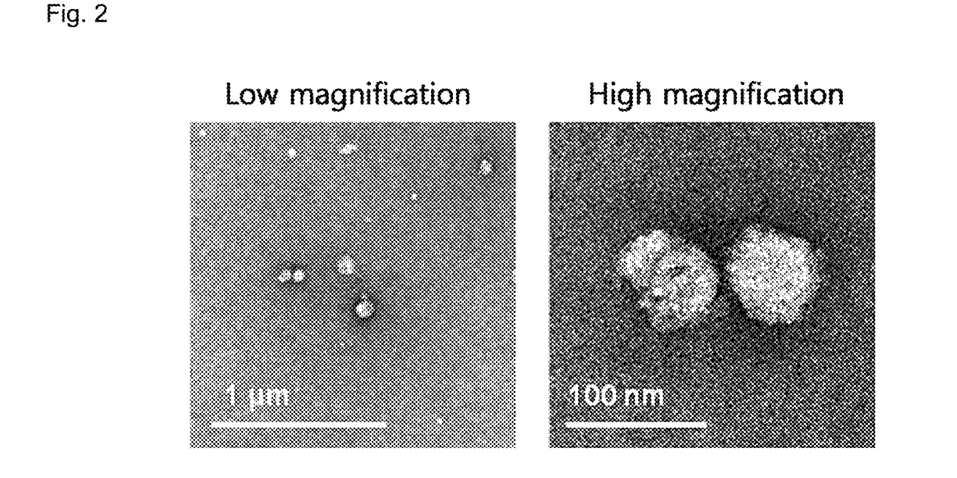
FIG. 2 shows transmission electron microscopic images of ginseng-derived exosome-like vesicles according to an exemplary embodiment of the present disclosure.

FIG. 2 shows the transmission electron microscopic images of the ginseng-derived exosome-like vesicles. It was confirmed that the ginseng-derived exosome-like vesicles had a diameter of 50-100 nm and were roughly spherical.

Test Example 2. Comparison of Melanin Production by MNT-1 Cells After Treating with Ginseng-Derived Exosome-Like Vesicles (1 μg/mL) for 1 week The human melanoma cell line MNT-1 cells were cultured in a minimum essential medium (MEM) supplemented with 20% fetal bovine serum under the condition of 37° C. and 5% $CO_2$. After plating the cells on a 60-mm culture dish with $1 \times 10^5$ cells per dish and waiting overnight, the medium was replaced with the same medium to which 1 μg/mL of the ginseng-derived exosome-like vesicles obtained in Example 1 were added. For comparison, a negative control group was treated with nothing. The fresh medium containing the exosome-like vesicles was replaced once in 4 days and the cells were cultured for a total of 8 days until they filled the dish. When the cells were fully grown, they were treated with 300 μL of a lysis buffer (1% NP-40, 50 mM Tris-HCl; pH 7.5, 150 mM NaCl) and collected into a microtube using a cell scraper. Then, after centrifuging at 15,000 rpm for 10 minutes, the precipitating pellets were dissolved in 1 N NaOH and melanin contents were compared by measuring absorbance at 450 nm.

Figure 3:
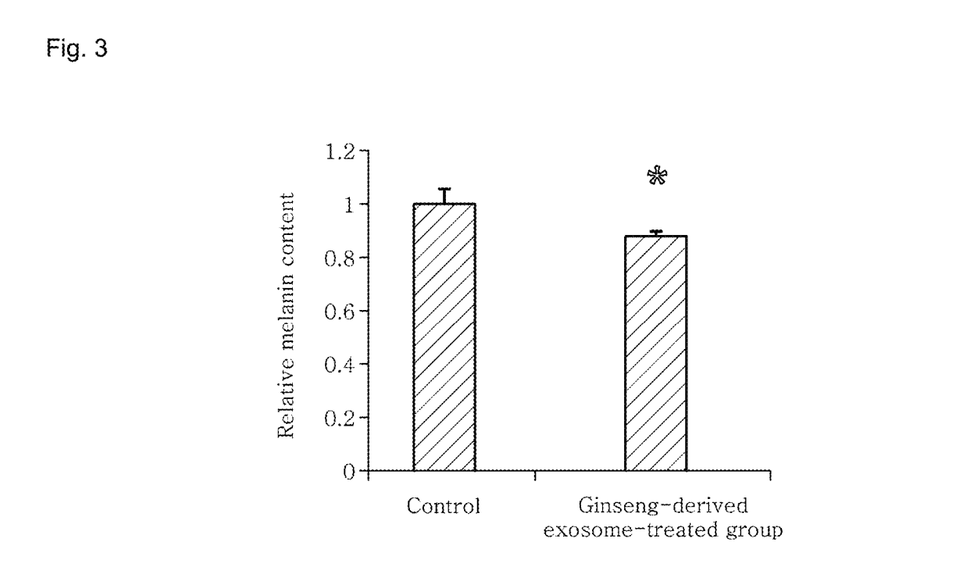
FIG. 3 shows melanin production by MNT-1 cells treated with ginseng-derived exosome-like vesicles according to an exemplary embodiment of the present disclosure.

As a result, it was confirmed that the melanin content decreased significantly in the MNT-1 cells treated with the ginseng-derived exosome-like vesicles as compared to the MNT-1 cells not treated with the ginseng-derived exosome-like vesicles, as seen from FIG. 3 (n=6, *: p<0.05).

Test Example 3. Comparison of Melanin Production by Human Melanocytes Irradiated with 20 mJ/cm$^2$ UVB 2 Times After Treating with Ginseng-Derived Exosome-Like Vesicles of Various Concentrations for 2 Weeks Human primary melanocytes (Life Technologies, CA, USA) were cultured in M-254 medium (Gibco BRL, NY, USA) supplemented with human melanocyte growth supplement (HMGS; Gibco BRL, NY, USA) under the condition of 37° C. and 5% $CO_2$. After plating the cells on a 100-mm culture dish with 2×10$^5$ cells per dish and waiting overnight, 20 mJ/cm$^2$ UVB was radiated 2 times with a 24-hour interval. Then, the cells were cultured for 2 weeks while replacing the medium with one containing the ginseng-derived exosome-like vesicles obtained in Example 1 at concentrations of 0.1 μg/mL, 1 μg/m L, 5 μg/mL or 10 μg/mL once in 4 days. For comparison, positive control groups were treated with 30 μM Melasolv, 1 μM compound K or 2 ppm fermented saponin for 2 weeks in the same manner and melanin production was measured. As negative control groups, melanocytes not treated with UVB and melanocytes treated with UVB but not treated with the test substances were cultured in the same manner. 2 weeks later, the cells were detached from the culture dish and counted. The cells of the same number were collected into a microtube, lysed with a RIPA lysis buffer (Millipore, 20-188) and then centrifuged at 13,500 rpm for 30 minutes. The precipitating pellets were dissolved in 1 N NaOH and photographed for comparison of color. Melanin contents were compared by measuring absorbance at 450 nm.

Figure 4:
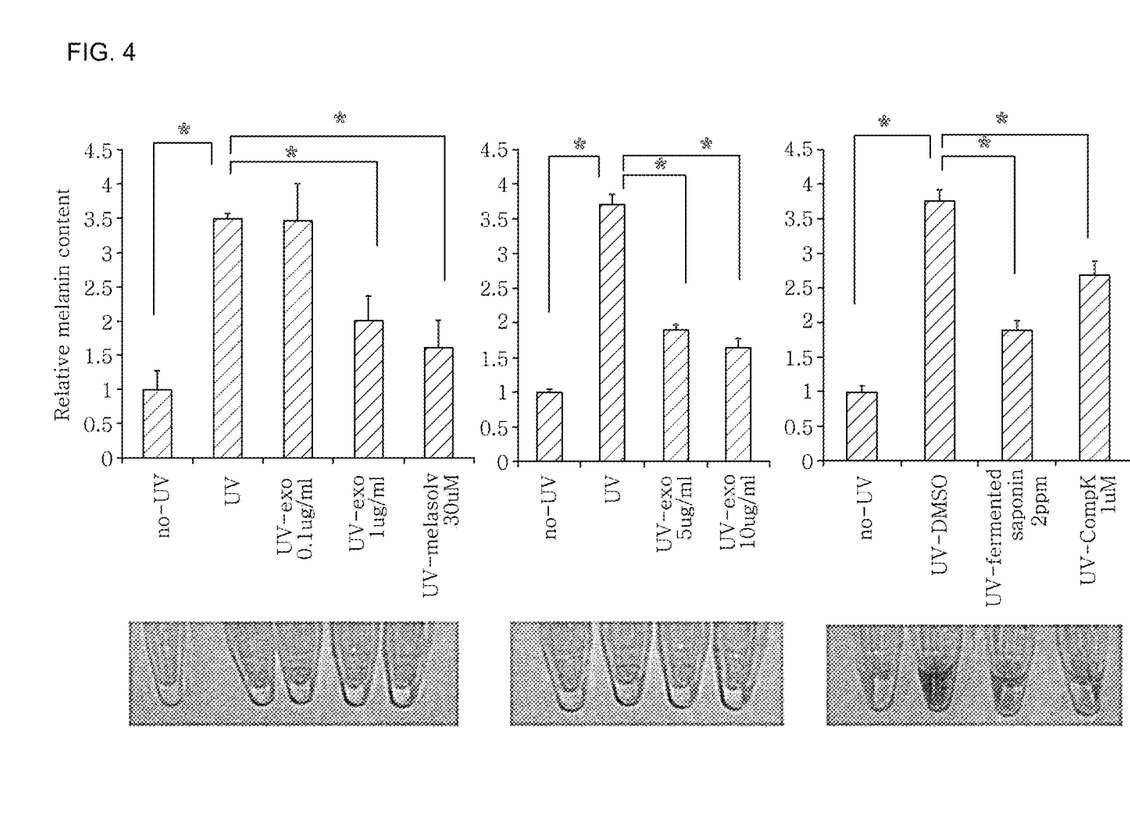
FIG. 4 compares melanin production by human melanocytes treated with ginseng-derived exosome-like vesicles according to an exemplary embodiment of the present disclosure or positive control substances (Melasolv (AmorePacific's representative skin whitening substance), compound K and fermented saponin).

As a result, it was confirmed that the melanin production increased by the UVB treatment was remarkably decreased when the cells were treated with 1 μg/mL or higher ginseng-derived exosome-like vesicles, as seen from FIG. 4 (*: p<0.05). The ginseng-derived exosome-like vesicles according to the present disclosure showed skin whitening effect comparable to those of AmorePacific's Melasolv, compound K and fermented saponin. The decrease in melanin contents when the cells were treated with the substances is shown in Table 1.

TABLE 1

Decrease (%) in melanin contents in human melanocytes irradiated with 20 mJ/cm$^2$ UVB 2 times after treating with test substances

| UV-exo 0.1 μg/mL | UV-exo 1 μg/mL | UV-Melasolv 30 μM | UV-exo 5 μg/mL | UV-exo 10 μg/mL | UV-fermented saponin 2 ppm | UV-Comp. K 1 μM |
|---|---|---|---|---|---|---|
| 1.1 | 42.6 | 54.0 | 48.5 | 55.7 | 49.8 | 28.3 |

Test Example 4. Comparison of Viability of Human Melanocytes 48 Hours After Treating with Ginseng-Derived Exosome-Like Vesicles or Ginseng Juice Human primary melanocytes (Life Technologies, CA, USA) were cultured in M-254 medium (Gibco BRL, NY, USA) supplemented with human melanocyte growth supplement (HMGS; Gibco BRL, NY, USA) under the condition of 37° C. and 5% $CO_2$. After plating 0.7×10$^5$ cells on a 24-well plate and waiting overnight, the medium was replaced with a medium containing the ginseng-derived exosome-like vesicles obtained in Example 1 (GEV) or ginseng juice at concentrations of 1 μg/mL or 10 μg/mL or a medium not containing them (control). After culturing for 48 hours, cell survivability was measured using the WST-1 solution (Roche Applied Science, Germany).

Figure 5:
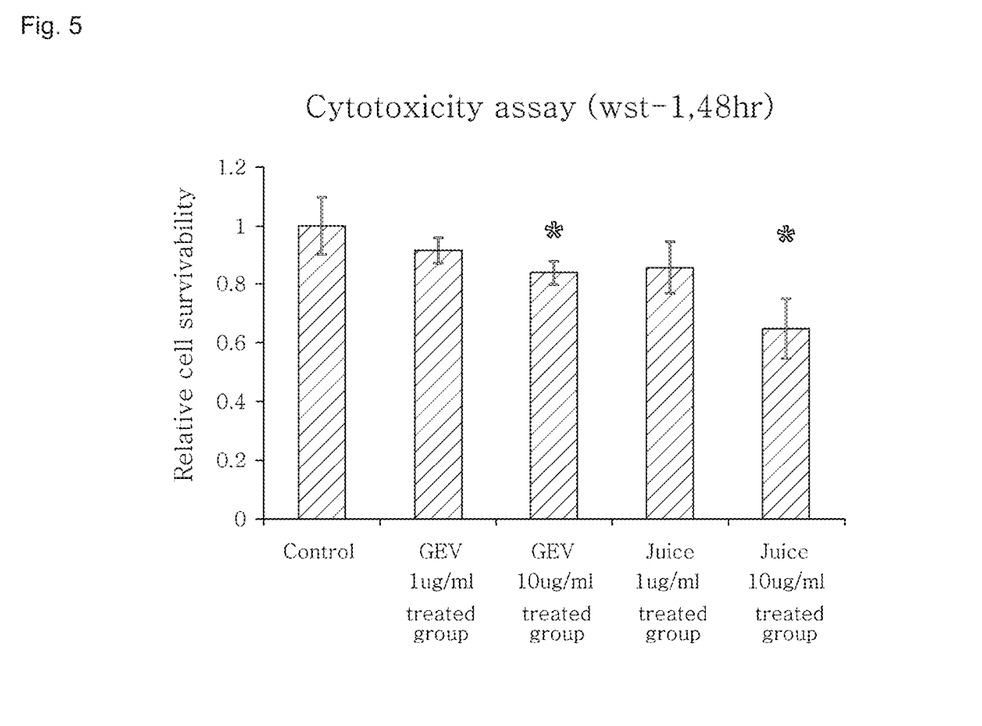
FIG. 5 compares the viability of human melanocytes treated with ginseng-derived exosome-like vesicles according to an exemplary embodiment of the present disclosure or ginseng juice.

As a result, the cell viability was 92% and 86%, respectively, when the ginseng-derived exosome-like vesicles (GEV) and ginseng juice were contained at a concentration of 1 μg/mL and the cell viability was 84% and 65%, respectively, when the ginseng-derived exosome-like vesicles (GEV) and ginseng juice were contained at a concentration of 10 μg/mL, as compared to the medium containing nothing (control), as seen from FIG. 5 (*: p<0.05). Accordingly, it was confirmed that the ginseng-derived exosome-like vesicles exhibit lower toxicity than the ginseng juice when treated at the same concentration.

Test Example 5. Comparison of Melanin Production by Human Melanocytes Irradiated with 20 mJ/cm$^2$ UVB 2 Times After Treating with Ginseng-Derived Exosome-Like Vesicles or Ginseng Juice for 2 Weeks Human primary melanocytes (Life Technologies, CA, USA) were cultured in M-254 medium (Gibco BRL, NY, USA) supplemented with human melanocyte growth supplement (HMGS; Gibco BRL, NY, USA) under the condition of 37° C. and 5% $CO_2$. After plating 2×10$^5$ cells on a 100-mm culture dish and waiting overnight, 20 mJ/cm$^2$ UVB was radiated 2 times with a 24-hour interval. Then, the cells were cultured for 2 weeks while replacing the medium with one containing the ginseng-derived exosome-like vesicles obtained in Example 1 or ginseng juice at concentrations of 1 μg/mL or 10 μg/mL once in 4 days. As control groups, melanocytes not treated with UVB and melanocytes treated with UVB but not treated with the test substances were cultured in the same manner. 2 weeks later, the cells were detached from the culture dish and counted. The cells of the same number were collected into a microtube, lysed with a RIPA lysis buffer (Millipore, 20-188) and then centrifuged at 13,500 rpm for 30 minutes. The precipitating pellets were dissolved in 1 N NaOH and photographed for comparison of color. Melanin contents were compared by measuring absorbance at 450 nm.

Figure 6:
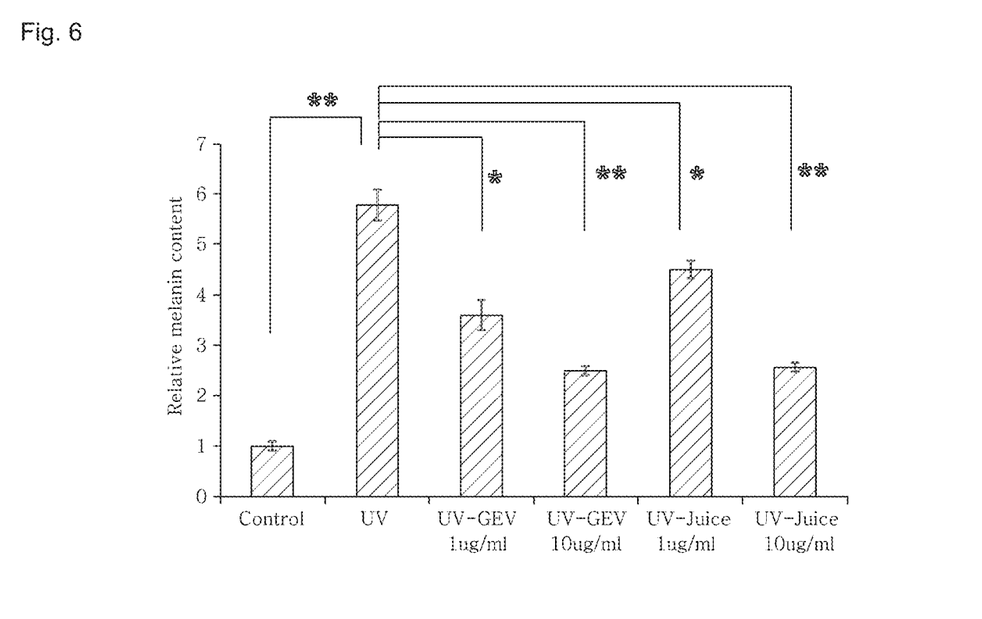
FIG. 6 compares melanin production by human melanocytes treated with ginseng-derived exosome-like vesicles according to an exemplary embodiment of the present disclosure or ginseng juice.

As a result, the melanin production increased by the UVB treatment was remarkably decreased when the cells were treated with the ginseng-derived exosome-like vesicles (GEV) or the ginseng juice, as seen from Table 2 and FIG. 6 (*: p<0.05, **: p<0.01). However, when considering that 10 μg/mL ginseng juice exhibits high cytotoxicity, it can be seen that the ginseng-derived exosome-like vesicles of the present disclosure can more effectively decrease the UV-induced increase in melanin content with low cytotoxicity.

TABLE 2

Decrease (%) in melanin contents in human melanocytes irradiated with 20 mJ/cm² UVB 2 times after treating with test substances

| UV-GEV 1 μg/mL | UV-GEV 10 μg/mL | UV-juice 1 μg/mL | UV-juice 10 μg/mL |
| --- | --- | --- | --- |
| 37.8 | 56.8 | 22.2 | 55.7 |

Hereinafter, the present disclosure will be described in detail through formulation examples. However, the following formulation examples are for illustrative purposes only and the scope of the present disclosure is not limited by the formulation examples.

[Formulation Example 1] Soft Capsule

A soft capsule was prepared by mixing 50 mg of ginseng-derived exosome-like vesicles, 80-140 mg of L-carnitine, 180 mg of soybean oil, 2 mg of palm oil, 8 mg of hydrogenated vegetable oil, 4 mg of yellow beeswax and 6 mg of lecithin and filling 400 mg per capsule according to a commonly employed method.

[Formulation Example 2] Tablet

A tablet was prepared by mixing 50 mg of ginseng-derived exosome-like vesicles, 200 mg of galactooligosaccharide, 60 mg of lactose and 140 mg of maltose, granulating the mixture using a fluidized-bed drier, adding 6 mg of sugar ester and then tableting using a tableting machine.

[Formulation Example 3] Granule

A granule was prepared by mixing 50 mg of ginseng-derived exosome-like vesicles, 250 mg of anhydrous crystalline glucose and 550 mg of starch, granulating the mixture using a fluidized-bed granulator and then filling in a pouch.

[Formulation Example 4] Drink

A drink was prepared by mixing 50 mg of ginseng-derived exosome-like vesicles, 10 g of glucose, 0.6 g of citric acid and 25 g of oligosaccharide syrup, adding 300 mL of purified water and filling 200 mL per bottle. After filling in the bottle, the drink was sterilized at 130° C. for 4-5 seconds.

[Formulation Example 5] Lotion

A lotion was prepared with the composition described in Table 3 according to a commonly employed method.

TABLE 3

| Ingredients | Contents (wt %) |
| --- | --- |
| ginseng-derived exosome-like vesicles | 2.00 |
| L-Ascorbic acid 2-phosphate magnesium salt | 1.00 |
| Water-soluble collagen (1% aqueous solution) | 1.00 |
| Sodium citrate | 0.10 |
| Citric acid | 0.05 |
| Licorice extract | 0.20 |
| 1,3-Butylene glycol | 3.00 |
| Purified water | balance |
| Total | 100.00 |

[Formulation Example 6] Cream

A cream was prepared with the composition described in Table 4 according to a commonly employed method.

TABLE 4

| Ingredients | Contents (wt %) |
| --- | --- |
| ginseng-derived exosome-like vesicles | 2.00 |
| Polyethylene glycol monostearate | 2.00 |
| Self-emulsifying glyceryl monostearate | 5.00 |
| Cetyl alcohol | 4.00 |
| Squalane | 6.00 |
| Glyceryl tri(2-ethylhexanoate) | 6.00 |
| Glycosphingolipid | 1.00 |
| 1,3-Butylene glycol | 7.00 |
| Purified water | balance |
| Total | 100.00 |

[Formulation Example 7] Pack

A pack was prepared with the composition described in Table 5 according to a commonly employed method.

TABLE 5

| Ingredients | Contents (wt %) |
| --- | --- |
| ginseng-derived exosome-like vesicles | 2.00 |
| Polyvinyl alcohol | 13.00 |
| L-Ascorbic acid 2-phosphate magnesium salt | 1.00 |
| Lauroyl hydroxyproline | 1.00 |
| Water-soluble collagen (1% aqueous solution) | 2.00 |
| 1,3-Butylene glycol | 3.00 |
| Ethanol | 5.00 |
| Purified water | balance |
| Total | 100.00 |

While the exemplary embodiments have been shown and described, it will be understood by those skilled in the art that various changes in form and details may be made thereto without departing from the spirit and scope of this disclosure as defined by the appended claims.

We claim:

1. A method for skin whitening, comprising administering an effective amount of an isolated ginseng-derived exosome-like vesicle for skin whitening to a subject in need thereof.

2. The method for skin whitening according to claim 1, wherein the exosome-like vesicle is isolated from *ginseng* root.

3. The method for skin whitening according to claim 1, wherein the exosome-like vesicle has a diameter of 20-500 nm.

4. The method for skin whitening according to claim 1, wherein the exosome-like vesicle is precipitated by ultracentrifugation of the extracellular fluid of *ginseng* at 100,000×g or higher.

5. The method for skin whitening according to claim 1, wherein the exosome-like vesicle has a buoyant density of 1.00-1.20 g/mL in iodixanol.

6. The method for skin whitening according to claim 1, wherein the exosome-like vesicle inhibits melanin production.

7. The method for skin whitening according to claim 1, wherein the exosome-like vesicle prevents, improves or treats one or more skin pigmentation disease selected from the group consisting of melasma, freckle, lentigo, nevus, melanoma, drug-induced pigmentation, post-inflammatory pigmentation and dermatitis-induced pigmentation.

8. A method for preparing an isolated ginseng-derived exosome-like vesicle, comprising:
   (1) a step of obtaining a juice by squeezing *ginseng*;
   (2) a step of centrifuging the juice and obtaining a supernatant by removing the remnant; and
   (3) a step of obtaining an exosome-like vesicle by ultracentrifuging the supernatant.

9. The method for preparing a ginseng-derived exosome-like vesicle according to claim 8, wherein the centrifugation in the step (2) is performed at 500-3,000×g for 10-30 minutes.

10. The method for preparing a ginseng-derived exosome-like vesicle according to claim 8, wherein the ultracentrifugation in the step (3) is performed using a sucrose cushion density gradient and an iodixanol density gradient.

11. The method for preparing a ginseng-derived exosome-like vesicle according to claim 8, wherein the ultracentrifugation in the step (3) is performed at 100,000-200,000×g for 1-6 hours.

12. The method for preparing a ginseng-derived exosome-like vesicle according to claim 8, wherein, in the step (3), the exosome-like vesicle is obtained by ultracentrifuging the supernatant and then separating a fraction having a buoyant density of 1.00-1.20 g/mL in iodixanol.

\* \* \* \* \*